(12) United States Patent
Bostic et al.

(10) Patent No.: US 11,071,454 B2
(45) Date of Patent: Jul. 27, 2021

(54) IDENTIFICATION OF DEVICE LOCATION IN HEALTHCARE FACILITY

(71) Applicant: Hill-Rom Services, Inc., Batesville, IN (US)

(72) Inventors: Dean Bostic, Batesville, IN (US); Ryan Hochworter, Batesville, IN (US); Eric P. Jensen, Niskayuna, NY (US)

(73) Assignee: HILL-ROM SERVICES, INC., Batesville, IN (US)

(*) Notice: Subject to any disclaimer, the term of this patent is extended or adjusted under 35 U.S.C. 154(b) by 0 days.

(21) Appl. No.: 16/722,573

(22) Filed: Dec. 20, 2019

(65) Prior Publication Data

US 2020/0205661 A1    Jul. 2, 2020

Related U.S. Application Data

(60) Provisional application No. 62/786,118, filed on Dec. 28, 2018.

(51) Int. Cl.
| | |
|---|---|
| G16H 40/20 | (2018.01) |
| G16H 10/65 | (2018.01) |
| H04W 4/30 | (2018.01) |
| H04W 4/80 | (2018.01) |
| A61G 7/05 | (2006.01) |
| G06Q 10/08 | (2012.01) |
| H04W 4/02 | (2018.01) |
| A61B 5/00 | (2006.01) |

(52) U.S. Cl.
CPC ............ A61B 5/002 (2013.01); A61G 7/05 (2013.01); G16H 10/65 (2018.01); G16H 40/20 (2018.01); H04W 4/025 (2013.01); H04W 4/30 (2018.02); H04W 4/80 (2018.02)

(58) Field of Classification Search
CPC ..................................................... A61B 5/002
See application file for complete search history.

(56) References Cited

U.S. PATENT DOCUMENTS

| 7,399,205 | B2 | 7/2008 | McNeely et al. |
| 8,499,108 | B2 | 7/2013 | Edwards et al. |
| 9,466,877 | B2 | 10/2016 | Dixon et al. |
| 9,830,424 | B2 | 11/2017 | Dixon et al. |
| 10,070,789 | B2 | 9/2018 | Collins, Jr. et al. |
| 2013/0103419 | A1* | 4/2013 | Beaudry ............... G16H 40/63 705/3 |

(Continued)

FOREIGN PATENT DOCUMENTS

EP        2767918 A2    8/2014

OTHER PUBLICATIONS

European Search Report, EP 19 21 9825, dated May 7, 2020, 7 pages.

*Primary Examiner* — Joseph H Feild
*Assistant Examiner* — Pameshanand Mahase
(74) *Attorney, Agent, or Firm* — Merchant & Gould P.C.

(57) ABSTRACT

A system for identifying a location of a device is described. The system includes a patient support device and a healthcare apparatus connected to the patient support device. The healthcare apparatus has a plurality of sensor devices and a scanner device. The scanner device is able to scan machine-readable labels to identify a patient identifier and a device identifier. A server is configured to determine a location of the patient support device using the patient identifier and device identifier.

20 Claims, 5 Drawing Sheets

(56) References Cited

U.S. PATENT DOCUMENTS

| | | | |
|---|---|---|---|
| 2014/0022080 A1* | 1/2014 | Mayoras, Jr. | A61B 5/6892 |
| | | | 340/573.1 |
| 2015/0128346 A1* | 5/2015 | Hollyoak | A61G 7/0509 |
| | | | 5/430 |
| 2016/0038361 A1* | 2/2016 | Bhimavarapu | A61G 7/018 |
| | | | 5/600 |
| 2016/0296143 A1* | 10/2016 | Hayes | A61B 5/0022 |
| 2018/0226141 A1* | 8/2018 | Slepian | G06Q 10/06 |
| 2019/0150737 A1* | 5/2019 | Bodurka | A61G 7/00 |

* cited by examiner

IDENTIFICATION OF DEVICE LOCATION IN HEALTHCARE FACILITY

BACKGROUND

The physical location of a device can be an important piece of information. In the healthcare context, medical devices, such as hospital beds, can include special features for the comfort and well-being of a patient. Identifying the location of a hospital bed within a healthcare facility can be important, particularly when a patient is in need of attention.

A real-time locating system (RTLS) can be used to automatically identify and track the location of a hospital bed. However, this type of system generally requires a fixed reference point such that the system is unable to identify the location of a hospital bed unless the hospital bed is properly connected to the fixed reference point. Further, such systems can be complex.

SUMMARY

One aspect relates to a system for identifying a location of a device. The system comprises a server connected to at least one of a healthcare apparatus and a patient support device. The server includes a processing device and at least one non-transitory computer readable data storage device storing instructions that, when executed by the processing device, cause the server to: receive inbound data including a patient identifier and a device identifier; correlate the device identifier to the patient identifier; receive location data associated with the patient identifier; determine a location of the patient support device based on correlating the location data to the device identifier; and transmit the location of the patient support device as outbound data to a status board.

Another aspect relates to a method for identifying a location of a device, the method comprising: receiving a patient identifier and a device identifier; correlating the device identifier to the patient identifier; receiving location data associated with the patient identifier; determining a location of the device by correlating the location data to the device identifier; and transmitting the location of the device to a status board.

Another aspect relates to a non-transitory computer readable storage device storing data instructions, which when executed by a processing device, cause the processing device to: receive a patient identifier and a device identifier; correlate the device identifier to the patient identifier; receive location data associated with the patient identifier; determine a location of a device by correlating the location data to the device identifier; and transmit the location of the device to a status board.

The details of one or more techniques are set forth in the accompanying drawings and the description below. Other features, objects, and advantages of these techniques will be apparent from the description, drawings, and claims.

DESCRIPTION OF THE FIGURES

The following drawing figures, which form a part of this application, are illustrative of described technology and are not meant to limit the scope of the disclosure in any manner.

DETAILED DESCRIPTION

The present application is directed to the determination of the location of a device within a building. In the example embodiments described herein, the device is a medical device, such as a patient support device. In some examples, the patient support device can be a hospital bed, lift and/or surgical table. In examples described herein, the patient support device is a hospital bed positioned within a healthcare facility having multiple floors and rooms. Although the example embodiments are described in the context of a healthcare facility having hospital beds and vital signs monitors, the principles of the present application are applicable to other types of scenarios and devices as well.

Examples of systems that can assist in locating medical devices, such as hospital beds, within a healthcare facility are provided in U.S. Pat. Nos. 7,399,205; 9,466,877; and 9,830,424. The entireties of these references are hereby incorporated by reference.

Figure 1:
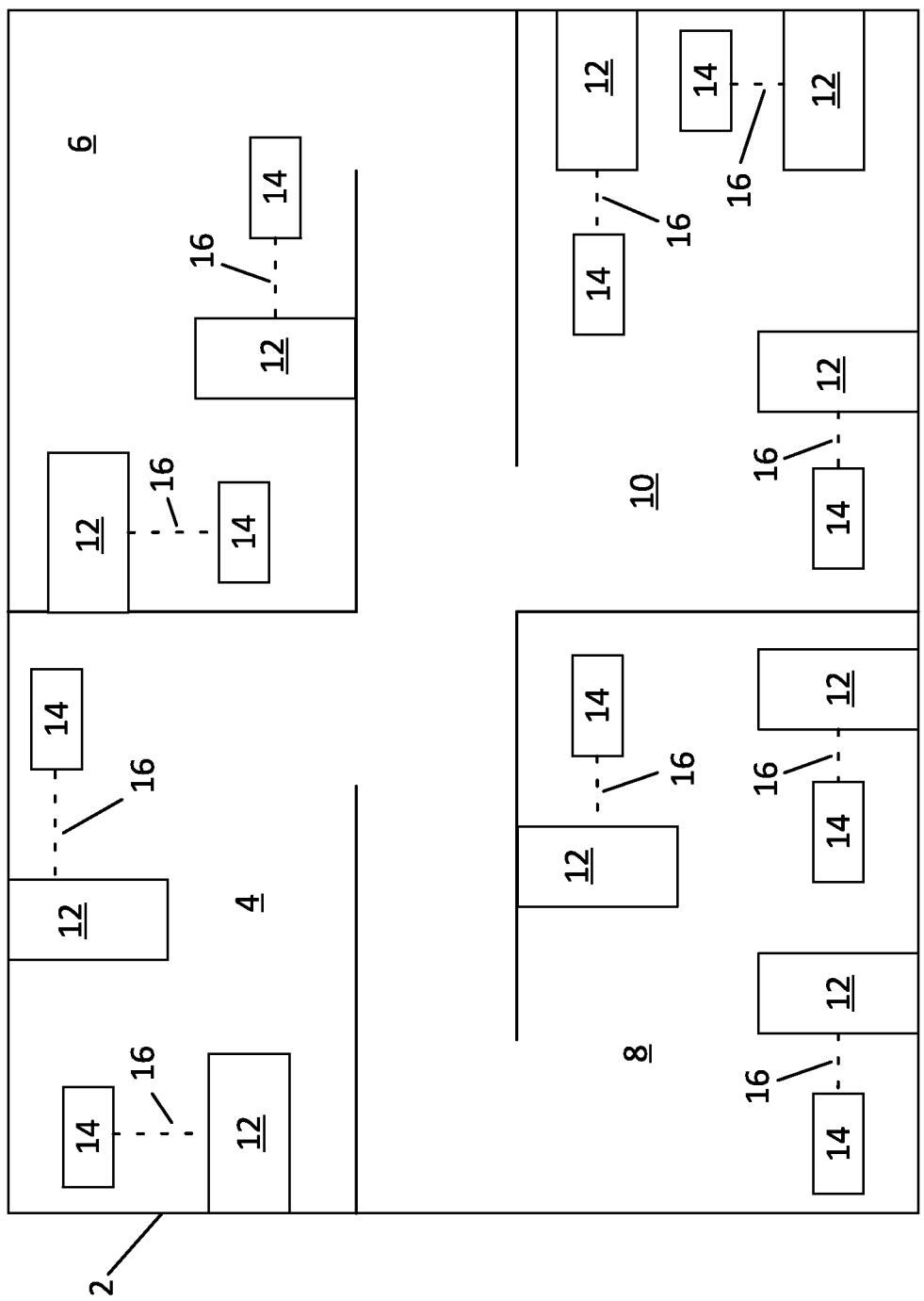
FIG. 1 is a schematic diagram of a healthcare facility.

FIG. 1 is a schematic diagram of a healthcare facility 2. Multiple rooms 4, 6, 8, 10 are arranged around a floorplan of the healthcare facility 2. Each room includes one or more hospital beds 12. Each hospital bed 12 may be similar to the hospital bed shown and described in U.S. Pat. No. 10,070,789, which is incorporated herein by reference in its entirety. As described herein, each hospital bed 12 may be considered a patient support device.

As further shown in FIG. 1, each room includes one or more vital signs monitors 14. Each vital signs monitor 14 may be similar to the healthcare apparatus shown and described in U.S. Pat. No. 8,499,108, which is incorporated herein by reference in its entirety. As described herein, each vital signs monitor 14 may be considered a healthcare apparatus.

Figure 2:
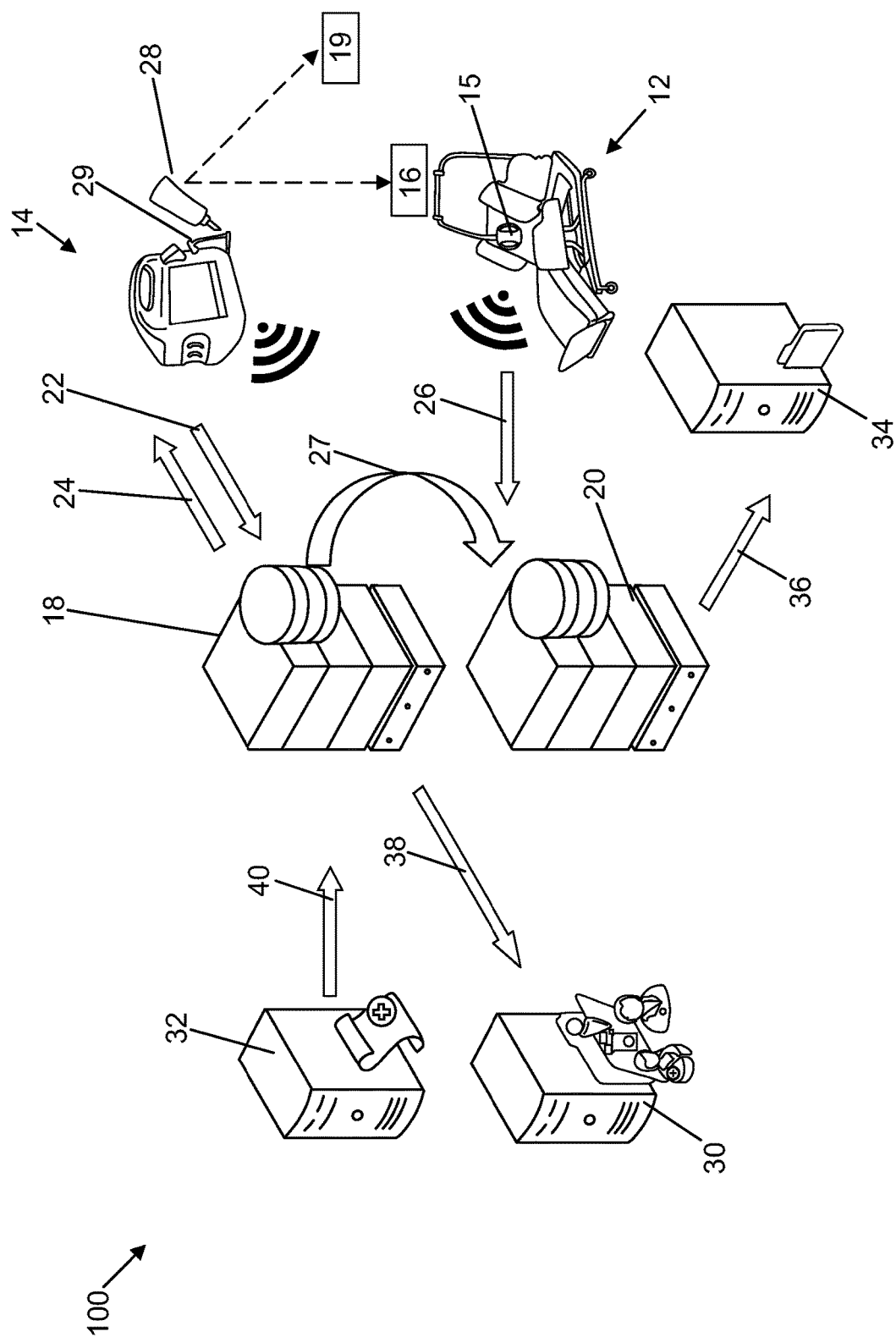
FIG. 2 is a schematic diagram of a system that can identify a location of a device.

FIG. 2 is schematic diagram of a system 100 that can identify a location of a device in the healthcare facility 2. As shown in FIG. 2, the system 100 includes a hospital bed 12 and a vital signs monitor 14. In the example depicted in FIG. 2, the vital signs monitor 14 is separate from the hospital bed 12. In such examples, the vital signs monitor 14 can be attached to a mobile stand (e.g., a stand having wheels that can be carted around the healthcare facility 2) or can be mounted to a wall or another device. Other configurations are possible.

In other examples, the vital signs monitor 14 is fixed to the hospital bed 12. The term "fixed" may include examples where the vital signs monitor 14 is connected to or plugged into the hospital bed 12 via a physical connection such as through one or more cables.

The system 100 includes a healthcare apparatus server 18 connected to the vital signs monitor 14. The healthcare apparatus server 18 includes a computing device that includes at least a processing device, and at least one non-transitory computer readable data storage device. In some examples, the healthcare apparatus server 18 is a Welch Allyn® Central Station (CS) Connex® server.

The healthcare apparatus server 18 is configured to receive inbound data 22 from the vital signs monitor 14. The healthcare apparatus server 18 is also configured to transmit outbound data 24 to the vital signs monitor 14. In some examples, the outbound data 24 includes computer executable instructions. In some examples, the vital signs monitor 14 is wirelessly connected to the healthcare apparatus server 18. As used throughout this disclosure, wireless connections can include cellular network connections, Bluetooth (including Bluetooth Low Energy (BLE)), Wi-Fi, radio-frequency identification (RFID), or Zigbee. Other configurations are possible. In other examples, the vital signs monitor 14 is connected to the healthcare apparatus server 18 via a cable connection such as through an Ethernet cable.

The vital signs monitor 14 includes a plurality of sensor devices 29. The sensor devices 29 can be used to measure one or more vital signs of a patient placed on the hospital bed 12. The one or more vital signs measured by the sensor devices 29 can be included in the inbound data 22 transmitted from the vital signs monitor 14 to the healthcare apparatus server 18.

The vital signs monitor 14 further includes a scanner device 28. The scanner device 28 is configured to scan a machine-readable label. In some examples, the machine-readable label is a bar code and the scanner device 28 is a bar code reader.

In some examples, a machine-readable label is located on a wristband worn by the patient. In such examples, the scanner device 28 can be used to scan the machine-readable label to identify a patient identifier 19. The patient identifier 19 is a unique set of numbers, letters and/or symbols that uniquely identifies the identity of the patient. In some examples, the patient identifier 19 is manually entered into the vital signs monitor 14 by a clinician using an input device such as a keyboard or touchscreen.

In examples where the vital signs monitor 14 is separate from the hospital bed 12, the scanner device 28 may also be used to scan a machine-readable label on the hospital bed 12 to identify a device identifier 16. The device identifier 16 uniquely identifies the hospital bed 12, and may include a unique set of numbers, letters, and/or symbols.

In further examples, the device identifier can be obtained by the vital signs monitor 14 through a wireless connection such as through a cellular network, Bluetooth (including Bluetooth Low Energy (BLE)), Wi-Fi, radio-frequency identification (RFID), or Zigbee connection. In some examples, the vital signs monitor 14 can obtain the device identifier 16 using an NFC antenna that receives the device identifier from a corresponding tag on the hospital bed 12. In other examples, the device identifier 16 is manually entered into the vital signs monitor 14 by a clinician using an input device such as a keyboard or touchscreen.

In examples where the vital signs monitor 14 is fixed to the hospital bed 12, the device identifier 16 may be stored in a memory of the vital signs monitor 14.

In addition to the vital signs measured from the sensor devices 29, the inbound data 22 may also include the patient identifier 19 and device identifier 16. As will be explained in more detail, the patient identifier 19 and device identifier 16 can be used to determine the location of the hospital bed 12 without requiring a fixed reference point in the healthcare facility 2.

As further shown in FIG. 2, the system 100 includes an EMR database 30. In some examples, the EMR database is a component of the healthcare apparatus server 18. In other examples, the EMR database 30 is externally connected to the healthcare apparatus server 18. For example, the EMR database 30 can be connected to the healthcare apparatus server 18 via a wireless connection in accordance with the above examples. In other examples, the EMR database 30 is connected to the healthcare apparatus server 18 via a cable connection. The EMR database 30 stores a plurality of Electronic Medical Records (EMRs). Each EMR contains the medical and treatment history of a patient admitted to the healthcare facility 2.

For example, the EMR of the patient placed on the hospital bed 12 can be stored in the EMR database 30. The vital signs measured from the sensor devices 29 of the vital signs monitor 14 are transmitted in the inbound data 22 to the healthcare apparatus server 18, and the healthcare apparatus server 18 transmits the measured vital signs as outbound data 38 for storage in the EMR database 30. The system 100 can thus automatically update the EMR of the patient admitted to the hospital bed 12.

As shown in FIG. 2, the system 100 includes an Admissions, Discharges, Transfers (ADT) server 32. The ADT server 32 is connected to the healthcare apparatus server 18 via a wireless connection in accordance with the above wireless examples. In other examples, the ADT server 32 is connected to the healthcare apparatus server 18 via a cable connection.

The ADT server 32 provides a real-time feed of ADT data 40 to the healthcare apparatus server 18. The ADT data 40 includes information on the status of each patient in the healthcare facility 2. For example, the ADT data 40 includes information such as the patient's name, the patient's location in the healthcare facility 2, his or her address, phone number, gender, and the like. The ADT data 40 includes information such as the date and time when the patient was admitted to the healthcare facility 2 and whether the patient was discharged from the healthcare facility 2. When the patient is discharged from the healthcare facility 2, the ADT data 40 includes information such as the date and time of the patient's discharge, and the patient's condition, diagnosis, etc. at the time of discharge.

Additionally, the ADT data 40 includes real-time location data of the patient in the healthcare facility 2. The location data can take the form of a set of numbers, letters, or symbols that identify the patient's assigned room number and floor number, as well as the geographical coordinates (e.g., latitude, longitude, and elevation) within the healthcare facility 2. The location data can also identify the name of the department, ward, care unit, and the like where the patient is admitted within the healthcare facility 2. The location data is updated each time the patient is moved within the healthcare facility 2 (e.g., each time the patient is transferred to a different room number, floor number, department, ward, care unit, etc.). As will be explained in more detail, the location data can be used to determine the location of the hospital bed 12 in the healthcare facility 2 without requiring a fixed reference point.

The system 100 further includes a patient support device server 20. As shown in FIG. 2, the hospital bed 12 is configured to transmit inbound data 26 to the patient support device server 20. In some examples, the hospital bed 12 is wirelessly connected to the patient support device server 20 in accordance with the above wireless examples. In other examples, the hospital bed 12 is connected to the patient support device server 20 via a cable connection. The patient support device server 20 has a computing device that includes at least a processing device, and at least one non-transitory computer readable data storage device. In some examples, the patient support device server 20 is a Hill-Rom® NaviCare® SmartSync server.

The hospital bed 12 can include one or more sensors 15 that detect and/or measure the weight and movement of a patient in the hospital bed 12. The weight and movement measurements detected by the one or more sensors 15 of the hospital bed 12 are included in the inbound data 26 transmitted from the hospital bed 12 to the patient support device server 20.

As further shown in FIG. 2, the system 100 includes a status board 34. The status board 34 is configured to receive outbound data 36 from the patient support device server 20. The outbound data 36 can include the weight and movement measurements detected by the one or more sensors 15 of the hospital bed 12. The status board 34 includes a display that can display outbound data 36 from the patient support device server 20. For example, the status board 34 can be a wall-mounted display that displays the outbound data 36. In some examples, the status board 34 can be a computer monitor. In some examples, the status board 34 can be a mobile computing device such as a smartphone, tablet computer, etc. that includes a display for displaying the outbound data 36. In some examples, the status board 34 is wirelessly connected to the patient support device server 20 in accordance with the above wireless examples. In other examples, the status board is connected to the patient support device server 20 via a wired connection.

As further shown in FIG. 2, the healthcare apparatus server 18 may also communicate with the patient support device server 20 through a connectivity 27. For example, the connectivity 27 can be a wireless connection in accordance with the above examples. In other examples, the connectivity 27 is a cable connection.

The connectivity 27 may supply data from the healthcare apparatus server 18 to the patient support device server 20. For example, the data transmitted through connectivity 27 may include the vital signs measured by the plurality of sensor devices 29 of the vital signs monitor 14. The data transmitted through connectivity 27 may also include the patient identifier 19 and/or the device identifier 16 scanned using the scanner device 28. Accordingly, the outbound data 36 transmitted from the patient support device server 20 may also include vital signs and the location of the hospital bed 12. As will be described in more detail, the location of the hospital bed can be calculated by using the patient identifier 19, device identifier 16, and the location data of the patient assigned to the hospital bed 12.

Figure 3:
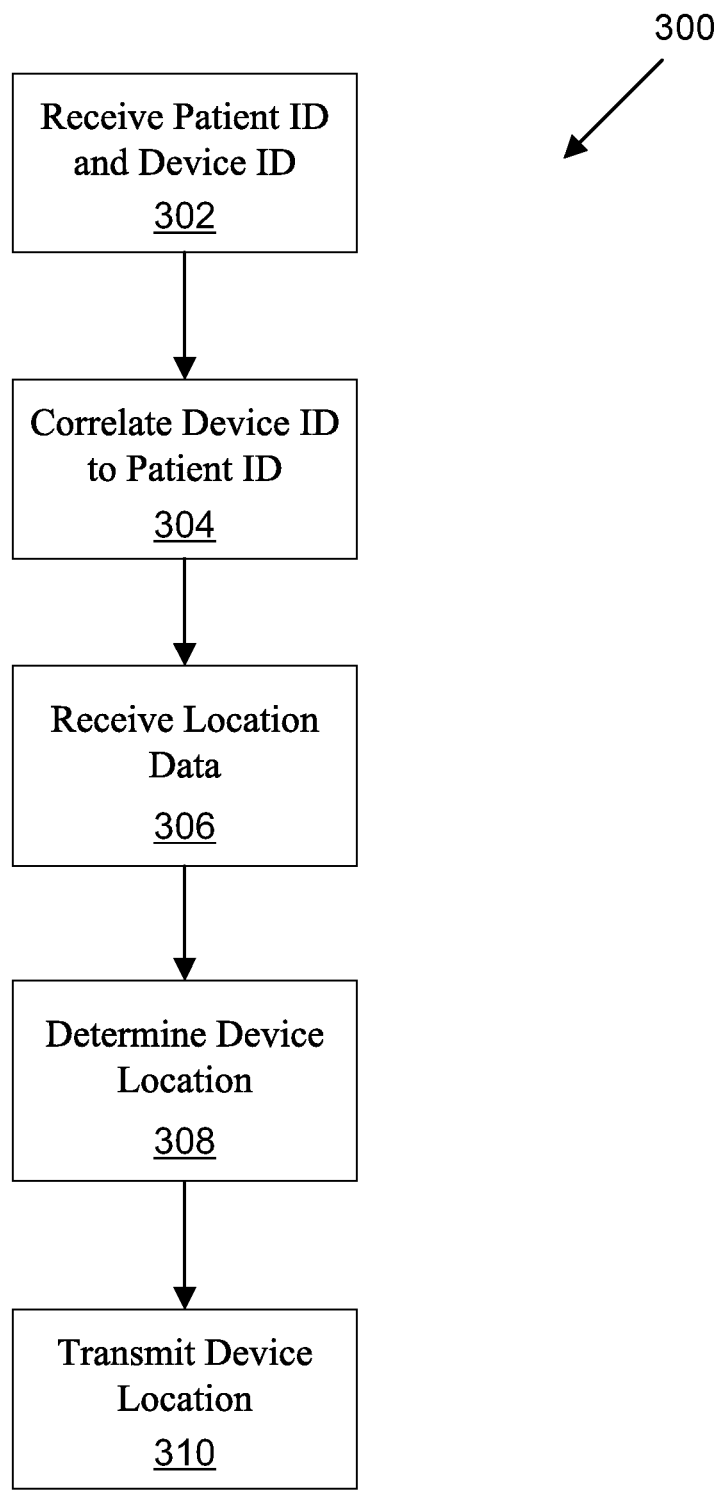
FIG. 3 illustrates a method of identifying a location of a device.

FIG. 3 illustrates a method 300 of identifying a location of a patient support device, such as the hospital bed 12, using a healthcare apparatus, such as the vital signs monitor 14, in the healthcare facility 2. As shown in FIG. 3, the method 300 includes a step 302 of receiving a patient identifier and device identifier in the form of inbound data from the healthcare apparatus. In some examples, the method 300 may also include transmitting outbound data to the healthcare apparatus. In some examples, the outbound data includes computer executable instructions.

The patient identifier identifies a patient placed on the patient support device, and the device identifier identifies the patient support device. In some examples, the healthcare apparatus is separate from the patient support device. In such examples, the healthcare apparatus can include a scanner device that can be used to scan machine-readable labels. In some examples, the machine-readable labels are bar codes and the scanner device is a bar code reader. A first machine-readable label can be located on a wristband worn by the patient placed on the patient support device, and can be used to identify the patient identifier. A second machine-readable label can be located on the patient support device, and can be used to identify the device identifier.

In further examples where the healthcare apparatus is separate from the patient support device, the healthcare apparatus obtains the device identifier using a wireless connection such as a cellular network connection, Bluetooth (including Bluetooth Low Energy (BLE)), Wi-Fi, radio-frequency identification (RFID), or Zigbee. In some examples, the healthcare apparatus obtains the device identifier using an NFC antenna that receives the device identifier from a corresponding tag on the patient support device. In other examples, the device identifier is manually entered into the healthcare apparatus by a clinician using an input device such as a keyboard or touchscreen. Other configurations are possible.

In some examples, the healthcare apparatus is fixed to the patient support device. In such examples, the device identifier may be stored in a memory of the healthcare apparatus.

Next, the method 300 includes a step 304 of correlating the device identifier to the patient identifier. The patient identifier identifies a patient associated with the patient support device while the device identifier identifies the patient support device. The patient's association with the patient support device is, for example, when a patient in a healthcare facility is admitted to a hospital bed.

Thereafter, the method 300 includes a step 306 of receiving location data associated with the patient identifier. The location data is received from an ADT server that provides a real-time feed of Admissions-Discharges-Transfers (ADT) data. The location data includes information such as a patient's assigned room number, floor number, department, ward, care unit, and the like.

Next, the method 300 includes a step 308 of correlating the location data to the device identifier to determine the location of the patient support device. The location data is associated with the patient identifier, and the device identifier is correlated to the patient identifier in step 304. Advantageously, by correlating the location data to the device identifier, the location of the patient support device is determined without requiring a fixed location point within a healthcare facility. Instead, the location of the patient support device is determined by the location data and the patient ID.

Thereafter, the method 300 includes a step 310 of transmitting the location of the patient support device. In some examples, the location of the patient support device is transmitted to a status board that displays the location of the patient support device. In some examples, the status board is fixed such as a wall mounted display or a computer monitor. In some examples, the status board is a mobile computing device such as a smartphone, tablet computer, etc.

In some examples, the method 300 is performed by the healthcare apparatus server 18. In other examples, the method 300 is performed by the patient support device server 20.

Figure 4:
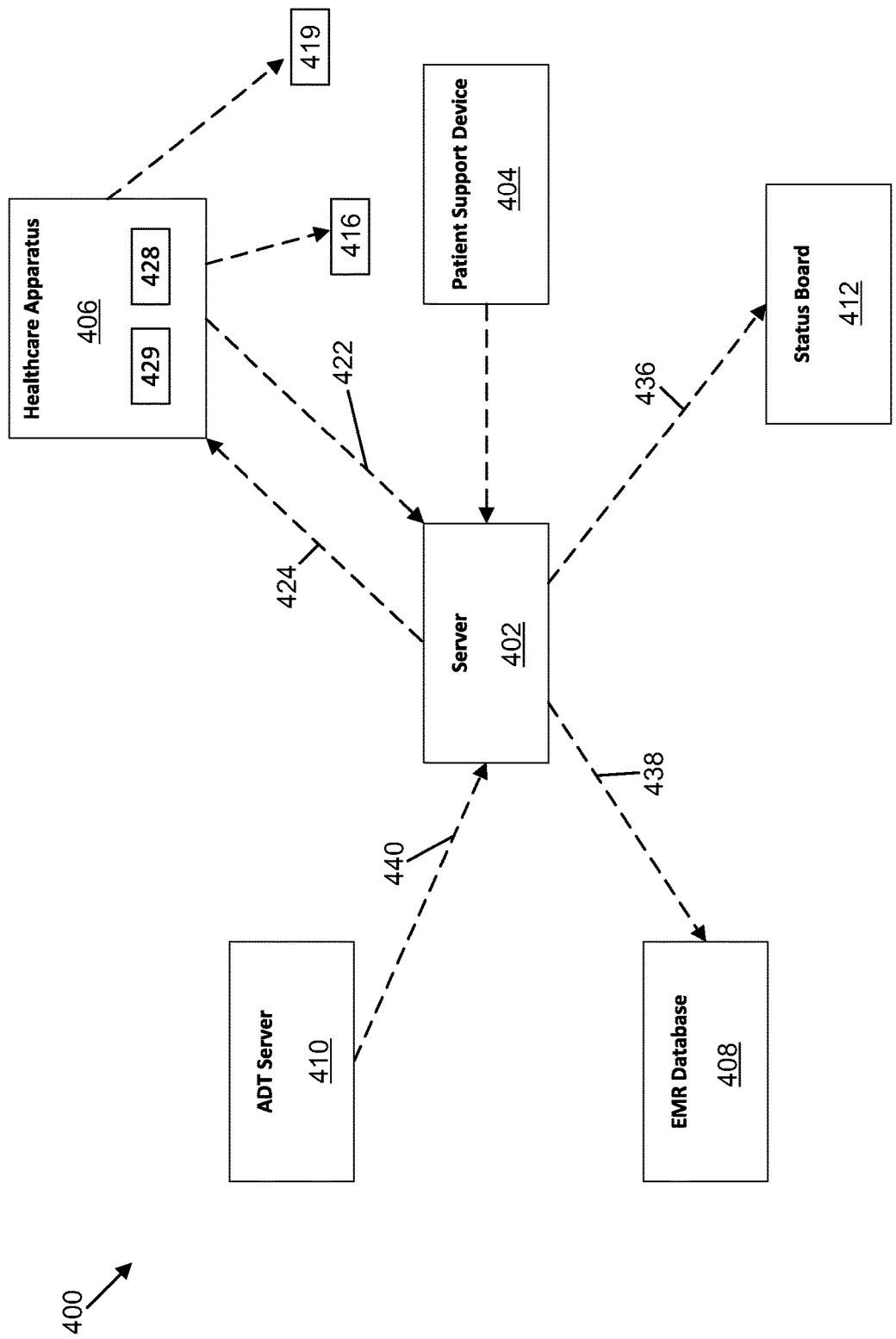
FIG. 4 is a schematic diagram of another system that can identify a location of a device.

FIG. 4 is a schematic diagram of another system 400 that can determine a location of a patient support device 404 using a healthcare apparatus 406. The system 400 is similar to the system 100 described above, but differs from the system 100 in that the healthcare apparatus serve 18 and the patient support device server 20 are combined into a single server 402 that performs the method 300 described above with reference to FIG. 3. The system 400 includes the server 402, a patient support device 404, and a healthcare apparatus 406.

The server 402 is configured to receive inbound data 422 from the healthcare apparatus 406. The server 402 is also configured to transmit outbound data 424 to the healthcare apparatus 406. In some examples, the outbound data 424 includes computer executable instructions The healthcare apparatus 406 includes a plurality of sensor devices 429. The sensor devices 429 can be used to measure one or more vital signs of a patient placed on the patient support device 404. The one or more vital signs measured by the sensor devices 429 are included in inbound data 422 transmitted from the healthcare apparatus 406 to the server 402.

The healthcare apparatus 406 further includes a scanner device 428. The scanner device 428 is configured to scan a machine-readable label. In some examples, the machine-readable label is a bar code and the scanner device 428 is a bar code reader.

In some examples, a machine-readable label is located on a wristband worn by the patient. In such examples, the scanner device 428 is used to scan the machine-readable label to identify a patient identifier 419. The patient identifier 419 is a unique set of numbers, letters or symbols that identifies the identity of the patient. In some examples, the patient identifier 419 is manually entered into the healthcare apparatus 406 using an input device such as a keyboard or touchscreen.

In the example shown in FIG. 4, the healthcare apparatus 406 is separate from the patient support device 404. In such examples, the scanner device 428 may also be used to scan a machine-readable label on the patient support device 404 to identify a device identifier 416. The device identifier 416 identifies the identity of the patient support device 404, and may include a unique set of numbers, letters, or symbols. In further examples, the device identifier 416 can be obtained by the healthcare apparatus 406 through a wireless connection such as through a cellular network, Bluetooth (including Bluetooth Low Energy (BLE)), Wi-Fi, radio-frequency identification (RFID), or Zigbee connection. In some examples, the healthcare apparatus 406 obtains the device identifier 416 using an NFC antenna that receives the device identifier from a corresponding tag on the patient support device 404. In other examples, the device identifier 416 is manually entered into the healthcare apparatus 406 by a clinician using an input device such as a keyboard or touchscreen.

In some examples, the healthcare apparatus 406 is fixed to the patient support device 404. In such examples, the device identifier 416 may be stored in a memory of the healthcare apparatus 406.

The system 400 further includes an EMR database 408. In some examples, the EMR database 408 is an internal component of the server 402. In other examples, the EMR database 408 is externally connected to the server 402 via a wireless or cable connection. The EMR database 408 stores a plurality of records. In some examples, vital signs measured from the healthcare apparatus 406 are transmitted to the server 402 in inbound data 422, and the server 402 transmits the measured vital signs as outbound data 438 for storage in the EMR database 408. Thus, the system 400 can automatically update the EMR of a patient.

As shown in FIG. 4, the system 400 further includes an ADT server 410. The ADT server 410 is connected to the server 402 via a wireless or cable connection. The ADT server 410 provides a real-time feed of Admissions-Discharges-Transfers (ADT) data 440 to the server 402.

The system 400 further includes a status board 412. The status board 412 is configured to receive and display outbound data 436 from the server 402. For example, the status board 412 can be a wall-mounted display that displays the outbound data 436. In some examples, the status board 412 can be a computer monitor. In some examples, the status board 412 can be a mobile computing device such as a smartphone, tablet computer, etc. that includes a display for displaying the outbound data 436. In some examples, the status board 412 is wirelessly connected to the server 402 in accordance with the above wireless examples. In other examples, the status board 412 is connected to the server 402 via a connection such as an Ethernet cable.

As described above, the server 402 can perform the method 300 such that the outbound data 436 can include the location of the patient support device 404. Thus, in accordance with the method 300, the location of the patient support device 404 is determined by the server 402 without requiring a fixed location point within a healthcare facility.

In some examples, the outbound data 436 can include additional information such as weight and movement measurements detected by one or more sensors of the patient support device 404. In some examples, the outbound data 436 can also include one or more vital signs measured by the sensor devices 429 of the healthcare apparatus 406.

Figure 5:
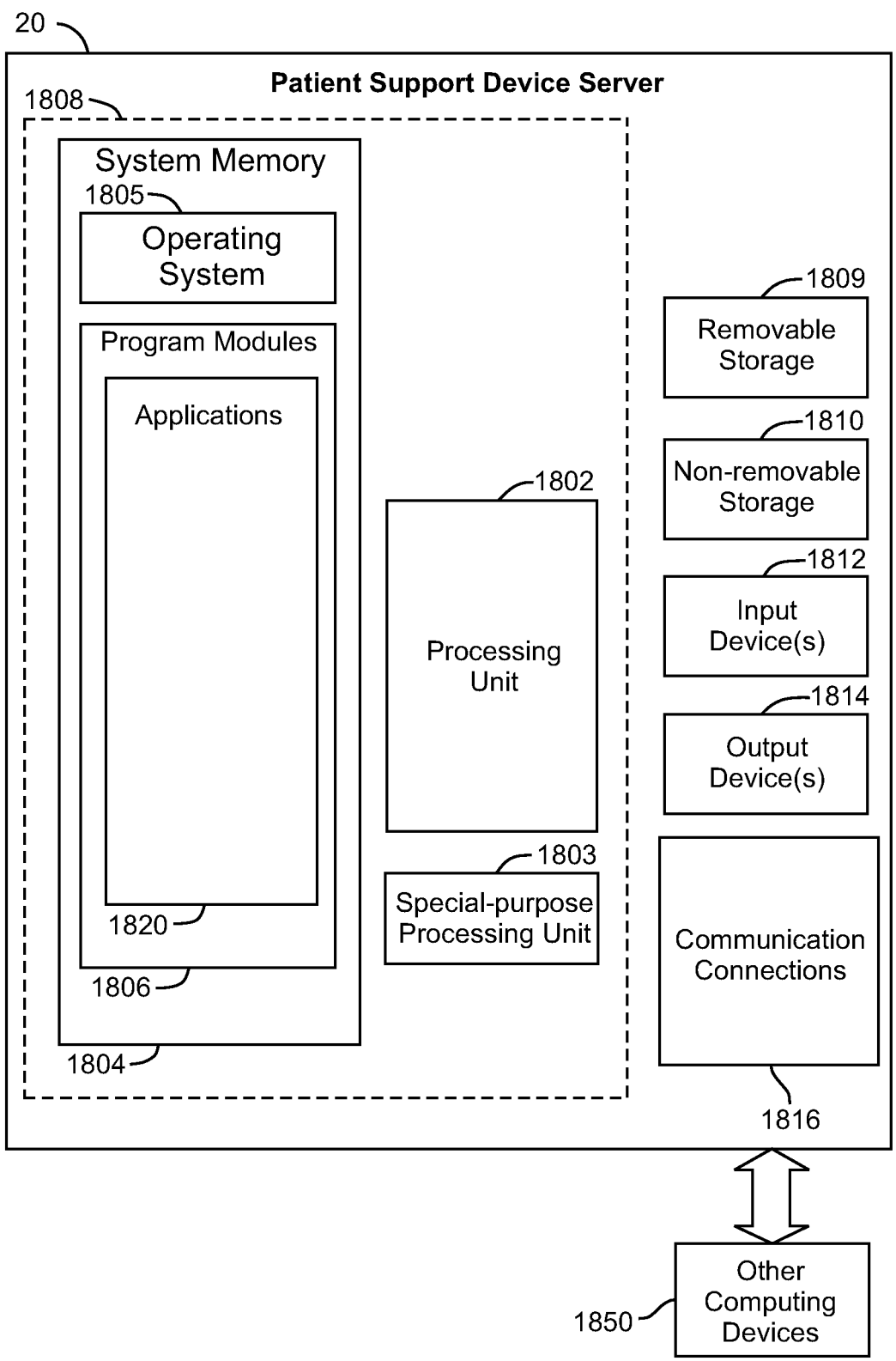
FIG. 5 is a block diagram illustrating physical components of a patient support device server.

FIG. 5 is a block diagram illustrating physical components (i.e., hardware) of the patient support device server 20. While the following components are described in the context of the patient support device server 20, these hardware components may be suitable for use in any of the other devices described above, including, but not limited to, the hospital bed 12, vital signs monitor 14, healthcare apparatus server 18, EMR database 30, ADT sever 32, status board 34, server 402, patient support device 404, healthcare apparatus 406, EMR database 408, ADT server 410, and status board 412.

In a basic configuration, the patient support device server 20 includes at least one processing unit 1802 and a system memory 1804. Depending on the configuration and type of computing device, the system memory 1804 may comprise, but is not limited to, volatile storage (e.g., random access memory), non-volatile storage (e.g., read-only memory), flash memory, or any combination of such memories.

The system memory 1804 may further include an operating system 1805 and one or more program modules 1806 suitable for running software applications 1820. The operating system 1805, for example, may be suitable for controlling the operation of the patient support device server 20. Embodiments of the disclosure may be practiced in conjunction with other operating systems, or other application programs and is not limited to any particular application or system.

This basic configuration of the patient support device server 20 is illustrated in FIG. 5 by those components within a dashed line 1808. The patient support device server 20 may have additional features or functionality. For example, the patient support device server 20 may also include additional data storage devices (removable and/or non-removable) such as, for example, magnetic disks, optical disks, or tape. Such additional storage is illustrated by a removable storage device 1809 and a non-removable storage device 1810. Furthermore, embodiments of the disclosure may be practiced in conjunction with a graphics library.

A number of program modules and data files may be stored in the system memory 1804. While executing on the at least one processing unit 1802, the program modules 1806 may perform processes including determine proximity of wireless computing devices, connect with wireless computing devices, transfer vital sign data to a patient's EMR, sort list of wireless computing devices within range, and other processes as described herein. Other program modules that may be used in accordance with embodiments of the present disclosure, and in particular to generate screen content, may include electronic mail and contacts applications, word processing applications, spreadsheet applications, database applications, slide presentation applications, drawing or computer-aided application programs, etc.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 5 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, may be operated via application-specific logic integrated with other components of the patient support device server 20 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

The patient support device server 20 may also have one or more input device(s) 1812, such as a keyboard, a mouse, a pen, a sound or voice input device, a touch or swipe input device, etc. Output device(s) 1814 such as a display, speakers, a printer, etc. may also be included. The aforementioned devices are examples and others may be used.

The patient support device server 20 may include one or more communication connections 1816 allowing communications with other computing devices. Examples of suitable communication connections 1816 include, but are not limited to, RF transmitter, receiver, and/or transceiver circuitry; universal serial bus (USB), parallel, and/or serial ports.

The term computer readable media as used herein may include non-transitory computer storage media. Computer storage media may include volatile and nonvolatile, removable and non-removable media implemented in any method or technology for storage of information, such as computer readable instructions, data structures, or program modules. The system memory 1804, the removable storage device 1809, and the non-removable storage device 1810 are all computer storage media examples (i.e., memory storage).

Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the patient support device server 20. Any such computer storage media may be part of the patient support device server 20. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, communication media may include wired media such as a wired network or direct-wired connection, and wireless media such as acoustic, radio frequency (RF), infrared, and other wireless media.

Although the example medical devices described herein are devices used to monitor patients, other types of medical devices can also be used. For example, the different components of the CONNEX™ system, such as the intermediary servers that communication with the monitoring devices, can also require maintenance in the form of firmware and software updates.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

It will be understood that those skilled in the art, both now and in the future, may make various improvements and enhancements can be made to the examples described herein.

The systems and method described herein result in a significant technical advantage. For example, the computing devices can be programmed to more efficiently determine the location of a hospital bed without requiring a fixed reference point.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features.

Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A system for identifying a location of a device, the system comprising:
   a server connected to at least one of a healthcare apparatus and a patient support device, the server having a processing device and at least one non-transitory computer readable data storage device storing instructions that, when executed by the processing device, cause the server to:
   receive inbound data including a patient identifier identifying a patient and a device identifier identifying the patient support device that is supporting the patient;
   correlate the device identifier to the patient identifier;
   receive location data associated with the patient identifier;
   determine a location of the patient support device based on correlating the location data to the device identifier, the location of the patient support device being determined without using a fixed reference point; and transmit the location of the patient support device as outbound data to a status board.

2. The system of claim 1, wherein the instructions cause the server to receive the patient identifier and the device identifier from the healthcare apparatus, and the healthcare apparatus includes a scanner device configured to scan machine-readable labels to identify the patient identifier and the device identifier.

3. The system of claim 1, wherein the inbound data further includes one or more vital signs of a patient placed on the patient support device, and the healthcare apparatus includes a plurality of sensor devices configured to measure the one or more vital signs.

4. The system of claim 3, wherein the plurality of sensor devices include one or more devices configured to measure blood pressure, pulse oximetry, temperature, capnography, and to provide respiratory monitoring and motion sensing.

5. The system of claim 3, wherein the instructions further cause the server to store the one or more vital signs to an electronic medical record database.

6. The system of claim 1, wherein the outbound data further includes weight and movement measurements detected by one or more sensors of the patient support device.

7. The system of claim 1, further comprising the patient support device, wherein the patient support device is a hospital bed.

8. The system of claim 1, further comprising the healthcare apparatus, wherein the healthcare apparatus is a vital signs monitor.

9. The system of claim 1, wherein the location data is received from an admissions, discharges, transfers (ADT) server configured to provide a real-time feed of admissions-discharges-transfers data.

10. A method for identifying a location of a device, the method comprising:

receiving a patient identifier identifying a patient and a device identifier identifying a device associated with the patient;

correlating the device identifier to the patient identifier;

receiving location data associated with the patient identifier;

determining a location of the device by correlating the location data to the device identifier, the location of the device being determined without using a fixed reference point; and transmitting the location of the device to a status board.

11. The method of claim 10, wherein the method is performed by a patient support device server, and the patient support device server receives the patient identifier and the device identifier as inbound data, and transmits outbound data including the location of the device to the status board.

12. The method of claim 11, wherein the device is a hospital bed.

13. The method of claim 10, further comprising receiving inbound data from a healthcare apparatus, the inbound data including the patient identifier, the device identifier, and one or more vital signs, and transmitting the one or more vital signs to an electronic medical record database.

14. The method of claim 13, wherein the patient identifier and the device identifier are obtained using a scanner device of the healthcare apparatus to scan machine-readable labels.

15. The method of claim 13, wherein the device identifier is obtained using an antenna of the healthcare apparatus to wirelessly receive the device identifier from a patient support device.

16. The method of claim 10, wherein the location data is received from an admissions, discharges, transfers (ADT) server configured to provide a real-time feed of admissions-discharges-transfers data.

17. A non-transitory computer readable storage device storing data instructions, which when executed by a processing device, cause the processing device to:

receive a patient identifier identifying a patient and a device identifier identifying a patient support device that is supporting the patient;

correlate the device identifier to the patient identifier;

receive location data associated with the patient identifier;

determine a location of the patient support device by correlating the location data to the device identifier, the location of the patient support device being determined without using a fixed reference point; and transmit the location of the patient support device to a status board.

18. The computer readable storage device of claim 17, wherein the non-transitory computer readable storage device is stored in a patient support device server, and the patient support device server receives the patient identifier and the device identifier as inbound data, and transmits outbound data including the location of the patient support device to the status board.

19. The computer readable storage device of claim 17, wherein the instructions further cause the processing device to receive inbound data from a healthcare apparatus, the inbound data including the patient identifier, the device identifier, and one or more vital signs, and transmitting the one or more vital signs to an electronic medical record database.

20. The computer readable storage device of claim 17, wherein the patient support device is a hospital bed.

* * * * *